United States Patent [19]

Osborn, III et al.

[11] Patent Number: 4,917,697
[45] Date of Patent: Apr. 17, 1990

[54] SANITARY NAPKINS HAVING FLAPS AND STRESS RELIEF MEANS

[75] Inventors: Thomas W. Osborn, III, Cincinnati; Letha M. Hines, Wyoming, both of Ohio

[73] Assignee: The Procter & Gamble Company, Cincinnati, Ohio

[21] Appl. No.: 175,814

[22] Filed: Mar. 31, 1988

[51] Int. Cl.$^4$ .............................................. A61F 13/16
[52] U.S. Cl. ...................... 604/387; 604/389
[58] Field of Search .................. 604/389, 385.1, 385.2, 604/386, 397, 398, 387

[56] References Cited

U.S. PATENT DOCUMENTS

| | | | |
|---|---|---|---|
| 3,397,697 | 8/1968 | Rickard | 604/370 |
| 4,285,343 | 8/1981 | McNair | 128/287 |
| 4,327,732 | 5/1982 | Thinnes | 128/290 R |
| 4,589,876 | 5/1987 | Van Tilburg | 604/385 R |
| 4,605,404 | 8/1986 | Sneider | 604/385 |
| 4,608,047 | 8/1986 | Mattingly | 604/387 |
| 4,687,478 | 8/1987 | Van Tilburg | 604/387 |
| 4,701,178 | 10/1987 | Glaug et al. | 604/387 |
| 4,759,754 | 7/1988 | Korpman | 604/387 |

FOREIGN PATENT DOCUMENTS

| | | |
|---|---|---|
| 1491234 | 4/1969 | Fed. Rep. of Germany . |
| 3319421 | 11/1984 | Fed. Rep. of Germany . |
| 0249924 | 12/1987 | United Kingdom . |

*Primary Examiner*—C. Fred Rosenbaum
*Assistant Examiner*—Mark O. Polutta
*Attorney, Agent, or Firm*—Larry L. Huston; John M. Pollaro; Fredrick H. Braun

[57] ABSTRACT

In accordance with the present invention, a sanitary napkin having flaps and a stress relief means for relieving the stresses that develop in the flaps when the flaps are folded down along the edges of the wearer's panties in the crotch, is provided. The flaps are associated with an absorbent means along a line of juncture. The stress relief means can be provided along the line of juncture or in the flaps. Two preferred stress relief means are a notch and a slit.

9 Claims, 4 Drawing Sheets

SANITARY NAPKINS HAVING FLAPS AND STRESS RELIEF MEANS

BACKGROUND OF THE INVENTION

1. FIELD OF THE INVENTION

The present invention relates to disposable absorbent articles and more particularly to female sanitary napkins. Particularly, the present invention concerns sanitary napkins having flaps and a stress relief means for relieving the stresses that develop in the flaps when the flaps are folded down and under a wearer's undergarment.

2. BACKGROUND ART

All manner and variety of absorbent articles configured for the absorption of body fluids such as menses, urine, and feces are, of course, well known. Particularly, sanitary napkins having flaps are disclosed in the literature and are available in the marketplace.

Generally, the flaps extend laterally from a central absorbent means and are intended to drape over the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of the general type described are disclosed in U.S. Pat. No. 4,687,478, entitled "Shaped Sanitary Napkin With Flaps", which patent issued to Van Tilburg on Aug. 18, 1987, U.S. Pat. No. 4,608,047, entitled "Sanitary Napkin Attachment Means", which patent issued to Mattingly on Aug. 26, 1986, U.S. Pat. No. 4,589,876, entitled "Sanitary Napkin", which patent issued to Van Tilburg on May 20, 1986, U.S. Pat. No. 4,285,343, entitled "Sanitary Napkin", which patent issued to McNair on Aug. 25, 1981, U.S. Pat. No. 3,397,697, entitled "Disposable Sanitary Shield For Undergarments", which patent issued to Rickard on Aug. 20, 1968, and U.S. Pat. No. 2,787,271, entitled "Sanitary Napkin", which patent issued to Clark on Apr. 2, 1957.

While sanitary napkins having flaps are commonly viewed as providing better protection soiling as compared to sanitary napkins without flaps, the flapped napkins commonly experience a problem that keeps them from being optimally effective. The problem is that the flaps sometimes become detached from the underside of the wearer's panties.

When the flaps are folded down along the edges of the wearer's panties, stresses are created in the flaps. The stresses are especially high along the fold line at the edges of the wearer's panties where the flaps are bent from the bodyside of the panty to the underside of the panty. These stresses are magnified when a wearer sits or crouches because the edges of the panties are pulled outwards against the flaps thus increasing the forces against this fold line. When the stresses become too high, the flaps may become detached from the panty and some portion of the aforementioned benefits of the flaps may be lost. Thus, there is a commercial need for a way of eliminating or at least reducing the stresses that develop in the flaps when folded, so as to prevent them from becoming detached from the wearer's panties.

Therefore, it is an object of the present invention to provide a sanitary napkin having flaps and a stress relief means for relieving the stresses that develop in the flaps when they are folded down along the edges of the wearer's panties in the crotch and affixed to the underside of the panties.

It is an additional object of the present invention to provide a sanitary napkin having flaps wherein a slit is provided in the flaps or along the line of juncture between the flaps and the central absorbent means of the napkinn so as to relieve the stresses that develop in the flaps when they are folded.

It is an additional object of the present invention to provide a sanitary napkin having flaps wherein a notch is provided in the flaps or along the line of juncture between the flaps and the central absorbent means of the napkin so as to relieve the stresses that develop in the flaps when they are folded.

It is an additional object of the present invention to provide a sanitary napkin having flaps wherein at least one stress relief means is provided at each longitudinal side of each flap.

These and other objects of the present invention will be more readily apparent when considered in reference to the following description and when taken in conjunction with the accompanying drawings.

SUMMARY OF THE INVENTION

In accordance with the present invention, a sanitary napkin having flaps and a stress relief means for relieving the stresses that develop in the flaps when the flaps are folded down along the edges of the wearer's panties in the crotch, is provided. The flaps are associated with an absorbent means along a line of juncture. The stress relief means can be provided along the line of juncture or in the flaps. Two preferred stress relief means are a notch and a slit.

BRIEF DESCRIPTION OF THE DRAWINGS

Figue 6 is a top plan view of still another alternatively preferred sanitary napkin embodiment of the present invention.

DETAILED DESCRIPTION OF PREFERRED EMBODIMENTS

The present invention relates to absorbent articles, more particularly to female sanitary napkins, and in particular to sanitary napkins having flaps and a stress relief means for relieving the stresses that develop in the flaps when they are folded down along the edges of the wearer's panties in the crotch and attached to the underside of the panties.

As used herein, the term "sanitary napkin" refers to an article which is worn by females adjacent to the pudendal region and which is intended to absorb and contain the various exudates which are discharged from the body (e.g., blood menses, and urine) and which is intended to be discarded after a single use (i.e., it is not intended to be laundered or otherwise restored or reused.)

Figure 1:
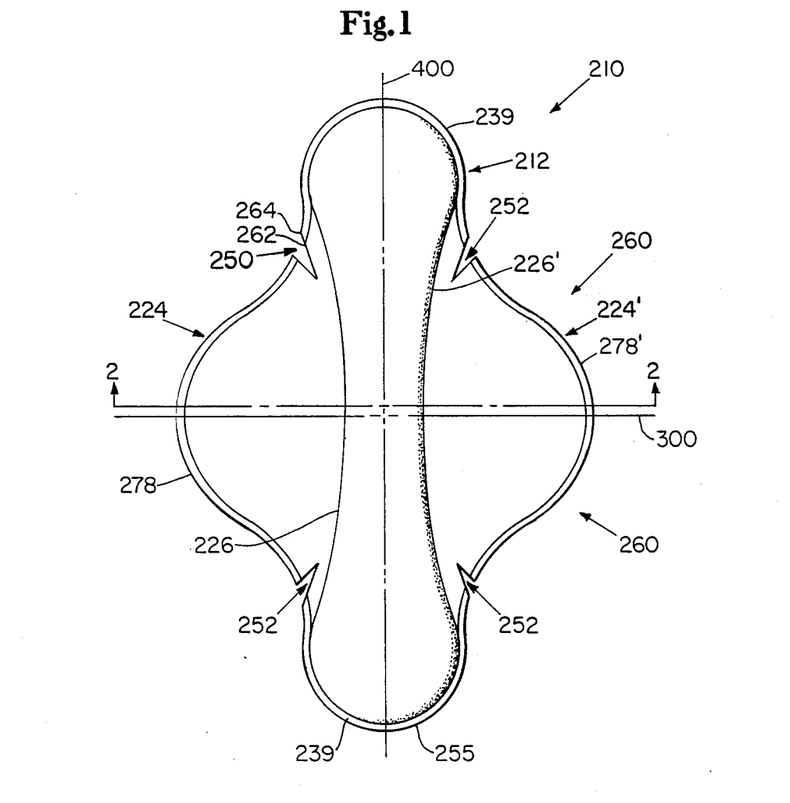
FIG. 1 is a top plan view of a preferred sanitary napkin embodiment of the present invention.

A preferred embodiment of a sanitary napkin 210 of the present invention is shown in FIG. 1. As seen in FIG. 1, a preferred sanitary napkin 210 basically comprises an absorbent means represented by central absorbent pad 212 and two flaps 224 and 224'. (In the discussion that follows, unless otherwise noted, the sanitary napkins will have two flaps. While it is not necessary that the napkins have two flaps, two flaps are preferred over one flap. Also, while it is not necessary that the flaps be mirror images of one another they preferably are. Thus, the description of one flap will be a description of the other, and, for clarity, discussion of the second flap will be omitted.)

Flap 224 is associated with central absorbent pad 212 along a line of juncture 226. As used herein, the term "line of juncture" refers to any of various curved or straight lines. Flap 224 has a distal edge 278 which is remote from the line of juncture 226. In the embodiment illustrated in FIG. 1, line of juncture 226 is concave relative to the distal edge 278. That is to say, line of juncture 226 curves away from distal edge 278. In this embodiment, lines of juncture 226 and 226' and seam 239 define an absorbent means (central absorbent pad 212) which is narrower in its central region than at its ends. A sanitary napkin narrower in the center than at the ends is generally perceived by the user as more comfortable than a sanitary napkin or uniform width.

Figure 2:
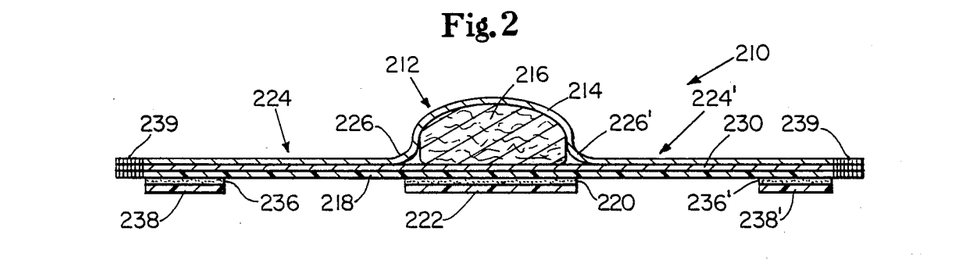
FIG. 2 is a lateral cross-sectional view of the preferred sanitary napkin embodiment shown in FIG. 1 taken along line 2—2 of FIG. 1.

FIG. 2, a cross-sectional view of sanitary napkin 210 taken along line 2—2 of FIG. 1, illustrates generally a preferred construction for sanitary napkin 210. As shown in FIG. 2, central absorbent pad 212 comprises absorbent core 216. Central absorbent pad 212 and flap 224 both comprise topsheet 214. Backsheet 218 is disposed on the side of absorbent core 216 and flap 224 opposite that of topsheet 214. In effect, topsheet 214 forms one surface of flap 224 while backsheet 218 forms the other surface; topsheet 214 also forms one surface of central absorbent pad 212, backsheet 218 the other.

In the embodiment illustrated, flap absorbent core 230 is interposed between topsheet 214 and backsheet 218. For simplicity of construction, flap absorbent core 230 extends throughout napkin 210 and is interposed between absorbent core 216 and backsheet 218. While this is a preferred embodiment primarily for reasons of construction, it is not necessary that flap absorbent core 230 be interposed between absorbent core 216 and backsheet 218.

Topsheet 214 and backsheet 218 are joined at seam 239 around the entire periphery of sanitary napkin 210. The purpose of this seam is to unite the various elements of the sanitary napkin into a whole. Topsheet 214 is secured to flap absorbent core 230 and backsheet 218 along lines of juncture 226 and 226' by attachment means not illustrated in FIG. 2.

Illustrated in FIG. 2 are the adhesive attachment means: central pad adhesive 220 and flap adhesive 236 which are covered by, respectively, central pad release liner 222 and flap release liner 238. These adhesive attachment means are adapted to secure sanitary napkin 210 within the crotch region of an undergarment.

Topsheet 214 is liquid permeable and, when sanitary napkin 210 is in use, is in close proximity to the skin of the user. Topsheet 214 is compliant, soft feeling, and non-irritating to the user's skin. It can be made from any of the materials conventional for this type of use. Non-limiting examples of suitable materials that can be used as topsheet 214 are woven and nonwoven polyester, polypropylene, nylon, and rayon and formed thermoplastic film with formed film being preferred. Suitable formed films are described in U.S. Pat. No. 3,929,135, entitled "Absorptive Structure Having Tapered Capillaries", which patent issued to Thompson on Dec. 30, 1975, U.S. Pat. No. 4,324,426, entitled "Disposable Absorbent Article Having A Stain-Resistant Topsheet", which patent issued to Mullane and Smith on Apr. 13, 1982, U.S. Pat. No. 4,342,314, entitled "Resilient Plastic Web Exhibiting Fiber-Like Properties", which patent issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which patent issued to Ahr, Louis, Mullane, and Ouellete on July 31, 1984, all of which patents are incorporated herein by reference. Formed films are preferred for topsheet 214 because they are pervious to liquids and yet non-absorbent. Thus, the surface of the formed film which is in contact with the body, remains dry and is more comfortable to the wearer.

In preferred embodiments of the present invention, the outer surface of topsheet 214 is treated with a surfactant. Treating the outer surface of the topsheet with surfactant renders the surface more hydrophilic which results in liquid penetrating the topsheet faster than if the surface were not treated. This diminishes the likelihood that menstrual fluids will flow off topsheet 214 rather than being absorbed by the absorbent core 216. It is preferred that the surfactant be substantially evenly and completely distributed across the outer surface of topsheet 214. This can be accomplished by any of the common techniques well known to those skilled in the art. For example, the surfactant can be supplied to topsheet 214 by spraying, by padding, or by the use of transfer rolls.

In preferred embodiments, the inner surface of topsheet 214 is secured in contacting relation to absorbent core 216. This contacting relationship results in liquid penetrating topsheet 214 faster than if it were not in contact with absorbent core 216. Topsheet 214 can be maintained in contact with absorbent core 216 by applying adhesive to the inner surface of the topsheet 214. Examples of suitable adhesives used for this purpose include the acrylic emulsion E-1833BT manufactured by Rohm and Haas Company of Philadelphia, Pa. and the acrylic emulsion WB 3805 manufactured by H. B. Fuller Company of St. Paul, Minn. The adhesives can be applied by the same methods as the surfactant is applied to the outer surface of topsheet 214.

Referring to FIG. 2, it can be seen that absorbent core 216 is positioned between topsheet 214 and backsheet 218. Absorbent core 216 provides the means for absorbing menstrual fluid. Absorbent core 216 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, absorbent hydrogel materials, polymeric fibers, or any equivalent material or combinations of materials.

Backsheet 218 is impervious to liquids and, thus, prevents menstrual fluid from soiling the clothing of the user. Any material used in the art for such purpose can be utilized herein. Suitable materials includes embossed or nonembossed polyethylene films and laminated tissue. A suitable polyethylene film is manufactured by Monsanto Chemical Corporation and marketed in the trade as Film No. 8020.

The portion of the outer surface of backsheet 218 which is generally in register with absorbent core 216 is coated with central pad adhesive 220. Central pad adhesive 220 provides an adhesive attachment means for securing central absorbent pad 212 in the crotch portion of a panty. Any adhesive or glue used in the art for such purpose can be used herein, with pressure-sensitive adhesive being preferred. Suitable adhesives are Century A-305-IV manufactured by the Century Adhesives Corporation and Instant LOK 34-2823 manufactured by National Starch Company. As shown in FIG. 2, central pad adhesive 220 may be the same width as absorbent core 216. However, the width is not critical and appropriate widths, as well as lengths, can be readily selected by those skilled in the art. The pressure-sensitive adhesive of central pad adhesive 220 should be covered with central pad release liner 222 to keep the adhesive from drying out and to keep it from sticking to extraneous surfaces prior to use. Any commercially available release liner commonly used for such purposes can be used herein. Nonlimiting examples of suitable release liners are BL 30 MG-A SILOX E1/0 and BL 30 MG-A SILOX 4 P/O both of which are manufactured by the Akrosil Corporation.

As can be observed from the foregoing discussion, central absorbent pad 212 is an absorbent means that has a fluid pervious body contacting surface (represented in FIG. 2 by topsheet 214) and an opposed liquid impervious surface (represented in FIG. 2 by backsheet 218). It is to be understood that the embodiment illustrated is only one possible embodiment, albeit a preferred one. Other possible embodiments include one in which an absorbent core is essentially completely wrapped with topsheet before it is placed on a backsheet. The absorbent means can also comprise an absorbent core which possesses sufficient integrity to stand alone and which is fluid permeable on one surface while the other surface has been treated to render it liquid impervious.

It should be noted that a narrow central absorbent pad 212 is effective because the overall configuration and use of sanitary napkin 210 results in central absorbent pad 212 being maintained in close proximity to the body. Such proximity of central absorbent pad 212 places it precisely where it should be: very near the body at the vaginal opening. Central absorbent pad 212 can then absorb the vast majority of the menstrual fluid (menses) before it has an opportunity to flow along the central absorbent pad 212.

It is to be observed that lines of juncture 226 and 226' are the lines along which flaps 224 and 224' are associated with the absorbent means (represented by central absorbent pad 212); as such they represent lines of demarcation between the absorbent means and the flaps. The lines of juncture can be concave, straight, or convex relative to distal edges 278 and 278' and relative to the bulk of central absorbent pad 212.

Central absorbent pad 212 may not have an absorbent capacity much greater than the total amount of menstrual fluid anticipated to be absorbed. Thus, central absorbent pad 212, in addition to being narrow, may be thin. Furthermore, a thin absorbent means is extremely comfortable to the user. In the embodiment illustrated in FIGS. 1 and 2, topsheet 214 serves as a topsheet for flaps 224 and 224'. In general, the flaps do not require a topsheet to enable them to function properly, but the use of a topsheet is preferred. Flap topsheets can be integral with the absorbent means' body contacting surface, as illustrated, or they can be independent elements; the former being preferred. All of the specific physical properties of the topsheet 214 previously described, apply to any flap topsheet that is used. There is, however, no requirement that the flap topsheet be the same material as the topsheet associated with the central absorbent pad. In preferred embodiments, the flat topsheet may be a nonwoven material while the topsheet over the central absorbent pad is a formed film.

Flap absorbent core 230 is positioned between topsheet 214 and backsheet 218, most importantly in flaps 224 and 224'. In the embodiment illustrated, flap absorbent core 230 also underlies absorbent core 216; this is a preferred arrangement because construction of the sanitary napkin 210 is thereby more easily facilitated. In this arrangement, the absorbent capacity of absorbent core 216 is enhanced. Flap absorbent core 230 provides a means for absorbing menstrual fluid that is not absorbed by, or that is expressed from, absorbent core 216. Flap absorbent core 230 is generally compressible, conformable, and non-irritating to the user's skin. It can be made from any of the materials that can be used to make the absorbent core 216 as described above. Preferably, flap absorbent core 230 is a tissue paper sheet. While the use of a flap absorbent core is highly preferred, it can be omitted.

In the embodiment illustrated in FIGS. 1 and 2, backsheet 218 serves as a backsheet for flaps 224 and 224'. The flaps require a backsheet (or more generally, a liquid impervious materials) to enable them to function properly. The flap backsheets can be integral with the absorbent means liquid impervious surface or they can be independent elements; the former being preferred. All of the specific physical properties of the backsheet 218 previously described apply to the flap backsheet.

The overall size of flap 224 can be readily selected by those skilled in the art. Preferably, sanitary napkin 210 is from about 10 to about 23 centimeters wide between distal edges 278 and 278' at their greatest separation. Preferably flap 224 is from about 5 to about 18 centimeters long in the direction parallel to the longitudinal axis of the sanitary napkin.

The outer surface of flap 224, adjacent distal edge 278, is coated with flap adhesive 236. Flap adhesive 236 is an adhesive attachment means which is used to assist in maintaining flap 234 in position after it is wrapped around the edge of the crotch portion of the panty as described below. Any adhesive used for central pad adhesive 220 can be used as flap adhesive 236. Also, flap adhesive 236 is covered with a removable flap release liner 238. Any release liner material used for central pad release liner 222 can be used for flap release liner 238.

As shown in FIGS. 1 and 2, topsheet 214 is secured to backsheet 218 along seam 239. Seam 239 can be formed by any means commonly used in the art for this purpose such as by gluing, crimping, or heat-sealing. Seam 239 is illustrated extending completely around the periphery of sanitary napkin 220; this is a preferred embodiment for ease of construction. (Other means of uniting the various elements can be used.) Flap absorbent core 230 is illustrated as extending into seam 239; this is, likewise in arrangement which results from a simplified construction technique.

The sanitary napkin shown in FIGS. 1 and 2 has a curvilinear line of juncture 226. As stated before, the absorbent core 216 is generally hourglass shaped so as to conform generally to the wearer's thighs. Thus, the line of juncture 226 between the flap 224 and the absorbent core 216 is curvilinear. However, sanitary napkins having an absorbent core having generally longitudinal edges, wherein the line of juncture between each flap and the longitudinal edges of the absorbent core is linear, can be easily constructed so that the sanitary napkin preferentially bends at the linear line of juncture of each flap and the longitudinal edge of the central absorbent core.

The precise shape of flap 224, as well as the overall shape of the sanitary napkin 210 can be selected by those skilled in the art without undue experimentation. In the preferred embodiment illustrated in FIG. 1, the flaps are symmetrically disposed along the longitudinal axis of the sanitary napkin; while this is a preferred embodiment, it is not a mandatory design feature.

Further, the sanitary napkin illustrated in FIG. 1 is an embodiment wherein the flaps are formed integrally with the topsheet and the backsheet of the sanitary napkin. Once again, while this is a preferred method of construction, it is not mandatory. Flaps and central absorbent means can be formed independently and joined by techniques well known to those skilled in the art in such a manner that the resulting sanitary napkin will function essentially equivalent to the embodiments illustrated herein.

Figure 3:
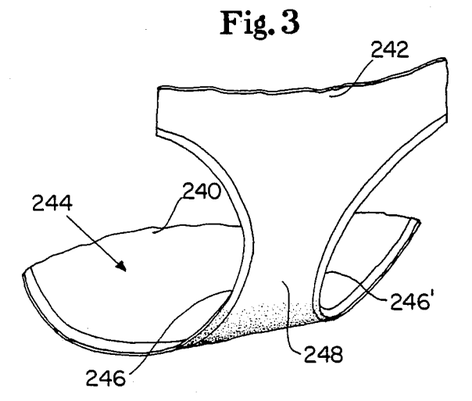
FIG. 3 is a perspective view of the crotch portion of a women's panties.

FIG. 3 is a depiction of the crotch portion 244 of an undergarment of the type commonly worn by many women and well known as a panty. A panty comprises a front section 240, a back section 242, and a crotch portion 244 which joins the front and back sections. The crotch portion 244 comprises two side edges 246 and 246' and center crotch portion 248.

Figure 4:
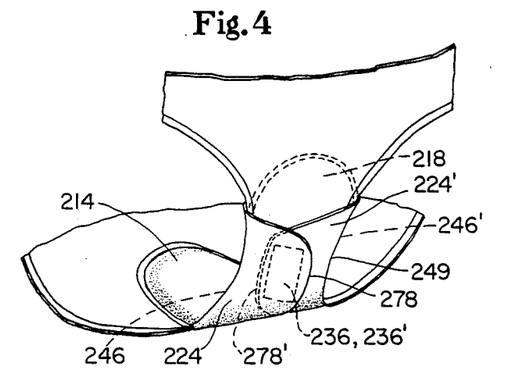
FIG. 4 is the same perspective view of the women's panties shown in FIG. 3 with the sanitary napkin embodiment of FIG. 1 being place therein for use.

The sanitary napkin of the present invention, such as the one illustrated in FIGS. 1 and 2, is utilized by removing the release liners 222 and 238 and 238' and thereafter placing the sanitary napkin in a panty as shown in FIG. 4. The center of central absorbent pad 212 is placed in crotch portion 244 of the panty with one end of central absorbent pad 212 extending towards the front section 240 of the panty and the other end towards the back section 242 and with the backsheet 218 in contact with the inner surface of center crotch portion 248 of the panty. Central pad adhesive 220 maintains central absorbent pad 212 in position. The distal portions of flaps 224 and 224' are folded around, respectively, side edges 246 and 246'. Flap adhesive 236 and 236' secure flaps 224 and 224' in such position. thus, flaps 224 and 224' are each folded over themselves with a portion of the panty, including side edges 246 and 246', interposed therebetween.

While a preferred sanitary napkin embodiment of the present invention has been described, numerous other sanitary napkin embodiments having flaps are available and are disclosed in the literature. In particular, sanitary napkins having flaps are disclosed in U.S. Pat. No. 4,687,478 entitled "Shaped Sanitary Napkin With Flaps", which patent issued to van Tilburg on Aug. 18, 1987, U.S. Pat. No. 4,608,047, entitled "Sanitary Napkin Attachment Means", which patent issued to Mattingly on Aug. 26, 1986, U.S. Pat. No. 4,589,876, entitled "Sanitary Napkin", which patent issued to Van Tilburg on May 20, 1986, U.S. Pat. No. 4,285,343, entitled "Sanitary Napkin", which patent issued to McNair on Aug. 25, 1981, U.S. Pat. No. 3,397,697, entitled "Disposable Sanitary Shield For Undergarments", which patent issued to Rickard on Aug. 20, 1968, and U.S. Pat. No. 2,787,241, entitled "Sanitary Napkin", which patent issued to Clark on Apr. 2, 1957, all of which patents are incorporated herein by reference.

Having now described a preferred sanitary napkin, the improvement which is the present invention will now be described. As mentioned previously, when the flap 224 is folded down along the edge 246 in the crotch portion 244 of the panty, stresses are developed in the flap 224. These stresses are magnified when the flap 224 is folded up under the panty and attached to the panty's underside. The stresses are further magnified when the panty is pulled up into position and the elastic in the panty edge 246 forces the flap 224 into the uppermost part of the wearer's crotch and thigh. The stresses are most highly concentrated along the fold 249 where the flap 224 changes from being on the bodyside of the panty to the underside of the panty, or in other words, at the edge 246 of the panty in the crotch portion 244. Thus, the concentrated stresses in the flap 224 generally follow the arc formed by the edge of the panty in the crotch portion 244. If the stresses are great enough, the flap 224 can become detached from the panty and the flap 224 becomes less than optimally effective. Depending on the design of the sanitary napkin, the arc of concentrated stresses may coincide with the line of juncture 226 between the flap 224 and absorbent means, but need not do so.

In order to eliminate, or at least reduce these stresses, the sanitary napkin is provided a first stress relief means 250. The first stress relief means 250 reduces the stresses along the fold 239 to such a degree that the flap 224 will remain attached to the underside of the panty.

Referring again to FIG. 1, a preferred first stress relief means 250 is the notch 252. As used herein, the term "notch" refers to a space, indentation, or hollow along the edge of a material or a laminate of materials. Another preferred first stress relief means 250 are the slits 254 shown in the alternative embodiment of a sanitary napkin 210 of the present invention shown in FIG. 5. As used herein, the term "slit" refers to a narrow cut wherein two edges of material are adjacent or nearly adjacent one another without being joined to one another. The slit 254 maybe linear or curvilinear.

Because of the numerous possible configurations for the sanitary napkin 210 and the flap 224, it is possible to say where on a particularly designed napkin the first stress relief means 250 should be without seeing that particular napkin in use. However, it has been determined through experimentation that the first stress relief means 250 preferably be located at a point where an edge of the napkin 210 intersects an edge 246 of the panty, in use. The points of intersection between the flap 224 and the edge 246 of the panty, which generally coincide with the ends of the fold 249, are the points where the first stress relief means 250 should preferably be located in order to reduce the stresses in the fold 249. Such first stress relief means 250 may be along the line of juncture 249 or outboard of the line of juncture 249 in the flaps 224 and 224'.

The points of intersection can generally be determined by having a model wear a particularly designed napkin having flaps and a fairly commonly designed panty. Commonly, panties have a crotch width of about 5.0 to about 7.5 centimeters. Marks can then be made on the bottom surface of the sanitary napkin 210 where the sanitary napkin 210 intersects the panty. Assuming the napkin has two flaps, the four marks will mark the general locations for the first stress relief means 250. Commonly, the first stress relief means 250 location will be between about 2.5 to about 7.5 centimeters (longitudinal dimension) from the lateral centerline 300 of the napkin 210.

Figure 5:
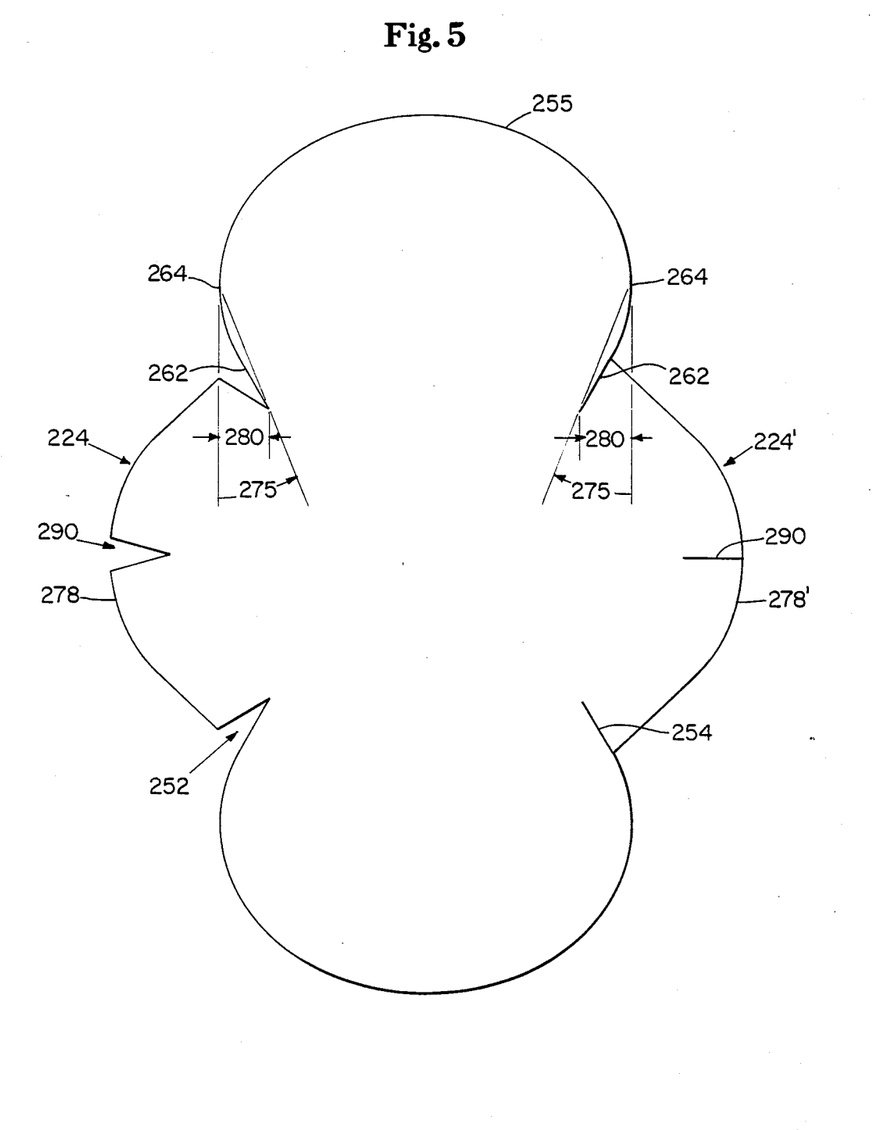
FIG. 5 is a top plan view of an alternatively preferred sanitary napkin embodiment of the present invention.

For illustration of the discussion that follows, FIG. 5 shows a preferred sanitary napkin 210 having flaps 224 and 224' wherein flap 224 has a pair of notches 252, and flap 224' has a pair of slits 254. Preferably, as shown in FIG. 5, each flap 224 and 224' has two first stress relief means 250, one on each side 260 of the lateral centerline 300 of the flap. Also, preferably, each pair of first stress relief means 250 at each flap 224 and 224' are symmetrical.

As seen in FIG. 5, the notches 252 and the slits 254 each having a leading edge 262. A leading edge 262 is the edge of a notch 252 or a slit 254, itself, which extends toward the central portion of the absorbent means. In the case of a notch which has two edges the leading edge 262 is the edge nearest the nearest end 255 of the napkin 210. If the edge of the notch 252 is jagged or the slit 254 is curvilinear or other configurations are present, a straight line approximation of a leading edge 252 is determined.

The leading edge 262 has an angle 275 measured from a longitudinal line which intersects the origination point 264 of the leading edge 262 and is parallel to the longitudinal centerline 400 of the napkin. Preferably, the angle 275 is from about 0° to about 145° from longitudinal, more preferably from about 0° to about 80° from longitudinal. The range from about 20° to about 40° from longitudinal. The range from about 20° to about 40° has been found to generally approximate the angle formed by the arc of the edge 246 of the panty in the crotch region 244 at the intersection of the flaps but the other preferred angles have been found to reduce stress, also.

The depth 280 of the leading edge 262 is measured perpendicularly from the time longitudional line as previously described and is preferably from about 2.0 to about 20.0 millimeters, more preferably from about 3.0 to about 12.0 millimeters, and most preferably from about 4.0 to about 9.0 millimeters.

As seen in FIG. 5, a second stress relief means 290 is provided along the distal edges 278 and 278' of the flap 224 and 224'. The second stress relief means 290 along the distal edge 278 of the flap 224 is a notch. The second stress relief means 290 along the distal edge 278' of the flap 224' is in the form of a slit. These second stress relief means 290 allow the flaps 224 and 224' to spread when the flaps are folded under the wearer's panties, thus reducing any tensile forces that may develop in the flaps. Preferably, these second stress relief means 290 are located along the lateral centerline 300 of the flaps. Preferably, these second stress relief means 290 extend from about 3.0 to about 30.0 millimeters inwards from the distal edges of the flaps.

Figure 6:
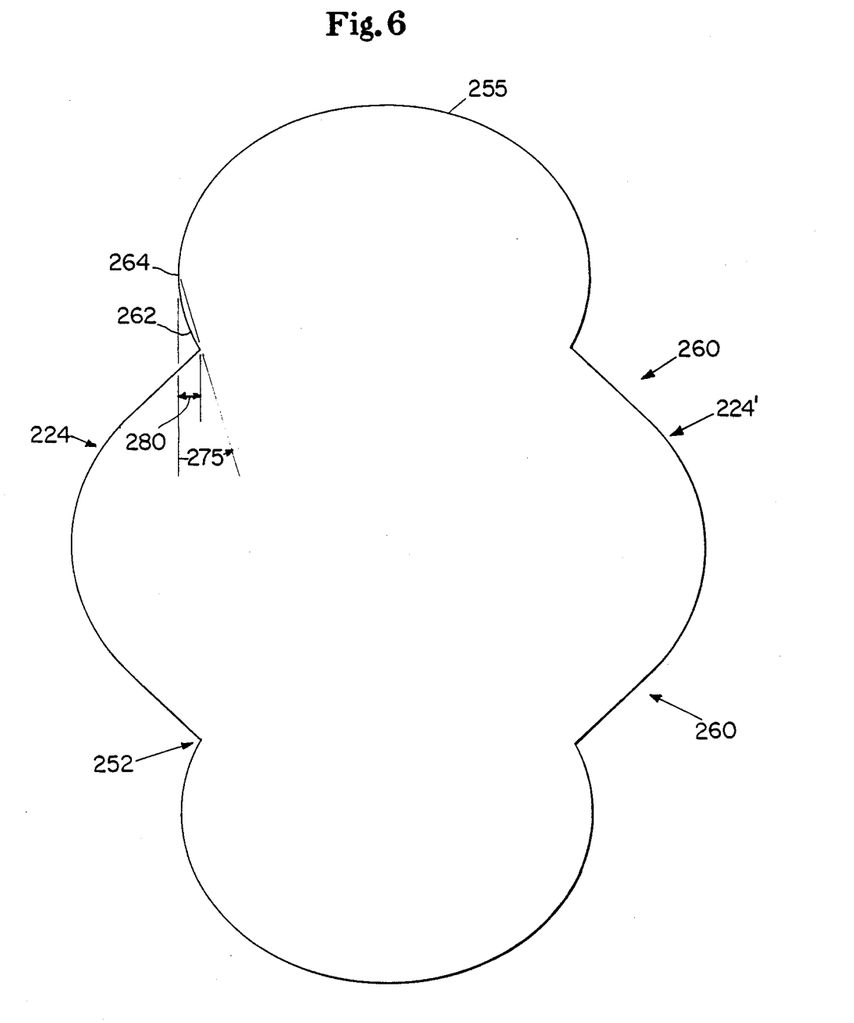

FIG. 6 is an alternative embodiment of a sanitary napkin 210 of the present invention having an alternatively preferred first stress relief means 250 in the form of a notch.

While particular embodiments of the present invention have been illustrated and described, it would be obvious to those skilled in the art that various other changes and modifications can be made without departing from the spirit and scope of the invention.

What is claimed is:

1. A sanitary napkin, comprising:
   an absorbent means;
   a flap associated with said absorbent means along a line of juncture and extending laterally outward from said absorbent means to a distal edge; and
   a first stress relief means for relief of stresses, said first stress relief means comprising a slit or a notch and being located along said line of juncture.

2. A sanitary napkin having a longitudinal centerline and a lateral centerline, said sanitary napkin comprising:
   an absorbent means:
   a flap associated with said absorbent means along a line of juncture and extending laterally outward from said absorbent means to a distal edge; and
   a first stress relief means for relief of stresses, said first stress relief means comprising a slit or a notch and being located in said flap remote from said line of juncture and said lateral centerline and intermediate said line of juncture and said lateral centerline.

3. A sanitary napkin as claimed in claims 1 or 2, wherein said flap has a first stress relief means on each side of said flap.

4. A sanitary napkin as claimed in claim 3, wherein said first stress relief means has a leading edge having an angle of from about 0° to about 145° from longitudinal.

5. A sanitary napkin as claimed in claim 3, wherein said first stress relief means has a depth of from about 2.0 to about 20.0 millimeters from longitudinal.

6. A sanitary napkin as claimed in claim 3, wherein said first stress relief means has a leading edge having an angle of from about 20° to about 40° from longitudinal.

7. A sanitary napkin as claimed in claim 6, wherein said first stress relief means has a depth of from about 3.0 to about 12.0 millimeters from longitudinal.

8. A sanitary napkin, comprising:
   an absorbent means;
   a flap associated with said absorbent means along a line of juncture and extending laterally outward from said absorbent means to a distal edge;
   a first stress relief means for relief of stresses, said first stress relief means comprising a slit or a notch and being located along said line of juncture; and
   a second stress relief means in said flap for relief of stresses which dvelop when said flap is folded down along the edges of a wearer's undergarments, said second stress relief means comprising a slit or a notch and being remote from said line of juncture.

9. A sanitary napkin as claimed in claim 8, wherein said flap has a lateral centerline and said second stress relief means is located along said lateral centerline of said flap.

* * * * *

UNITED STATES PATENT AND TRADEMARK OFFICE
CERTIFICATE OF CORRECTION

PATENT NO. : 4,917,697

DATED : April 17, 1990

INVENTOR(S) : Thomas W. Osborn, III and Letha M. Hines

It is certified that error appears in the above-identified patent and that said Letters Patent is hereby corrected as shown below:

Column 1, line 50, after "protection" insert --against--.

Column 2, line 13, reads "napkinn" should read --napkin--.

Column 3, line 35, reads "or" should read --of--.

Column 5, line 4, reads "includes" should read --include--.

Column 6, line 14, reads "flat" should read --flap--.

Column 6, line 37, reads "materials" should read --material--.

Column 7, line 64, reads "van" should read --Van--.

Column 8, line 50, reads "possible" should read --impossible--.

Column 9, line 28, reads "252" should read --262--.

Column 9, line 35, after "tudinal" insert --, and most preferably from about 20° to about 40° from longitudinal--.

Column 9, line 42, reads "time longitudional" should read --same longitudinal--.

Signed and Sealed this

Seventeenth Day of December, 1991

Attest:

HARRY F. MANBECK, JR.

*Attesting Officer*     *Commissioner of Patents and Trademarks*